United States Patent [19]

Goto et al.

[11] Patent Number: 4,695,398

[45] Date of Patent: Sep. 22, 1987

[54] CYCLOHEXANE DERIVATIVE

[75] Inventors: Yasuyuki Goto; Tetsuya Ogawa, both of Yokohama; Shigeru Sugimori, Fujisawa, all of Japan

[73] Assignee: Chisso Corporation, Osaka, Japan

[21] Appl. No.: 838,630

[22] Filed: Mar. 12, 1986

[30] Foreign Application Priority Data

Mar. 12, 1985 [JP] Japan .................... 60-48549

[51] Int. Cl.$^4$ .............. C09K 19/54; C09K 19/30; C07C 25/13
[52] U.S. Cl. ............... 252/299.5; 252/299.63; 350/350 R; 570/129; 570/182
[58] Field of Search ............ 252/299.5, 299.63; 350/350 R; 570/129, 182

[56] References Cited

U.S. PATENT DOCUMENTS

| 4,302,352 | 11/1981 | Eidenschink et al. | 252/299.63 |
| 4,405,488 | 9/1983 | Sugimori et al. | 252/299.63 |
| 4,415,470 | 11/1983 | Eidenschink et al. | 252/299.63 |
| 4,472,293 | 9/1984 | Sugimori et al. | 252/299.63 |
| 4,490,305 | 12/1984 | Eidenschink | 252/299.63 |
| 4,536,321 | 8/1985 | Sugimori et al. | 252/299.5 |
| 4,548,731 | 10/1985 | Sugimori et al. | 252/299.63 |
| 4,551,264 | 11/1985 | Eidenschine et al. | 252/299.63 |

FOREIGN PATENT DOCUMENTS

| 19665 | 12/1980 | European Pat. Off. | 252/299.63 |
| 3315295 | 10/1984 | Fed. Rep. of Germany | 252/299.61 |
| 55-118427 | 9/1980 | Japan | 252/299.63 |
| 59-42329 | 3/1984 | Japan | 252/299.63 |
| 59-59636 | 4/1984 | Japan | 252/299.66 |
| 59-170042 | 9/1984 | Japan | 252/299.63 |
| 60-54371 | 3/1985 | Japan | 252/299.61 |

OTHER PUBLICATIONS

Osmam, M. A. et al., Mol. Cryst. Liq. Cryst., vol. 82 (Lett), pp. 331-338 (1983).
CA., vol. 95(26):2258046 (1981).
CA. 90(15):121098e.
CA 89(1):5647p.

Primary Examiner—Teddy S. Gron
Attorney, Agent, or Firm—Fay, Sharpe, Beall, Fagan, Minnich & McKee

[57] ABSTRACT

A compound which, when used as a component of a liquid crystal composition, has an effectiveness of notably reducing the viscosity and the operating voltage of the resulting liquid crystal composition, and a liquid crystal composition containing the same are provided, which compound is a cyclohexane derivative expressed by the formula

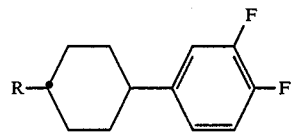

wherein R represents hydrogen atom or an alkyl group of 1 to 10 carbon atoms.

10 Claims, No Drawings

CYCLOHEXANE DERIVATIVE

BACKGROUND OF THE INVENTION

This invention relates to a novel cyclohexane derivative and a liquid crystal composition containing the same.

Display elements having liquid crystals applied therein utilize the optical anisotropy and dielectric anisotropy of liquid crystals, and they have various modes such as T-N (twisted nematic) type, DS (dynamic scattering) type, guest-host type, DAP type, etc., depending on their display modes. The properties required for liquid crystal substances used depending on these modes are varied respectively, but requirements common thereto consist in that the substances exhibit liquid crystal phases within as broad a temperature range as possible and also are stable to moisture, heat, liquid, air, etc. At present, however, there is no single compound which satisfies all of such requirements, and it is the present status that liquid crystal compositions obtained by blending several kinds of liquid crystal compounds or compounds similar to liquid crystals have been used.

Japanese patent application laid-open Nos. 55-118427/1980 and 59-170042/1984 disclose the following compounds:

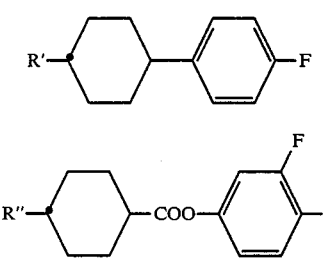

wherein R' represents an alkyl group of 1 to 12 carbon atoms and R' represents an alkyl group of 1 to 9 carbon atoms.

Any of these compounds exhibit no liquid crystal phase, but they are compounds similar to liquid crystals which can be used as a liquid crystal composition when blended with other liquid crystal compounds. However, the compounds of the formula (I) have a relatively low viscosity, but have a small dielectric anisotropy value Δε, while the compounds of the formula (II) have a relatively large dielectric anisotropy value Δε, but have a high viscosity. Thus either of these compounds have drawbacks.

SUMMARY OF THE INVENTION

The first object of the present invention is to provide a compound having a low viscosity and yet a large dielectric anisotropy value, and also is to provide a compound which, when blended with other compounds and used as a liquid crystal composition, has a good compatibility with the components and at least does not raise the viscosity and the driving voltage of the liquid crystal composition. The second object of the present invention is to provide a liquid crystal composition having a low viscosity and also a low operating threshold voltage.

The present invention have made extensive research and as a result have found a compound having superior physical properties suitable to the above objects, and a liquid crystal composition containing the same.

The present invention resides in
(1) a cyclohexane derivative expressed by the formula

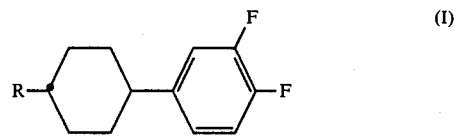

wherein R represents hydrogen atom or an alkyl group of 1 to 10 carbon atoms, and (2) a liquid crystal composition containing at least two components at least one of which is the cyclohexane derivative expressed by the above formula (I).

DESCRIPTION OF PREFERRED EMBODIMENTS

The compound expressed by the formula (I) may be prepared according to a known process as illustrated by the following reaction scheme:

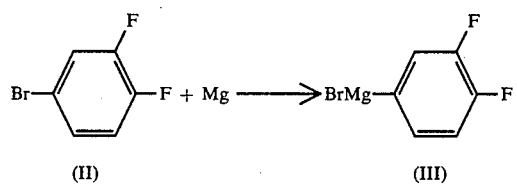

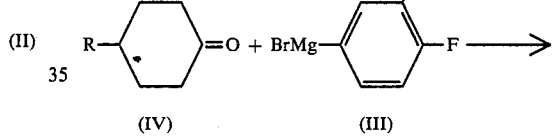

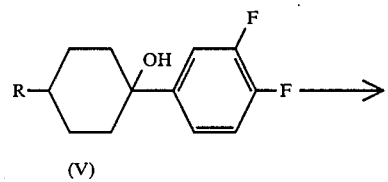

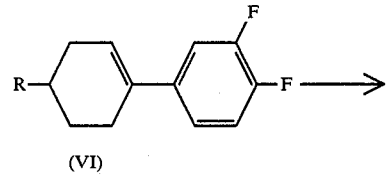

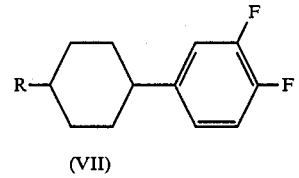

Namely, 3,4-diflurorbromobenzene (II) is reacted with Mg in a solvent such as tetrahydrofuran, diethyl ether, etc. to obtain 3,4-difluorophenylmagnesium bromide (III), which is then reacted with a 4-alkylcyclohexanone (IV) to obtain a 3,4-difluoro-(4-alkylcyclohexanon-1-ol) benzene (V), which is subjected to dehydration reaction with potassium hydrogen sulfate to obtain a 3,4-difluoro-(4-alkylcyclohexane-1-yl) benzene (VI), which is then subjected to a catalytic reduction reaction with hydrogen in the presence of a Raney Ni catalyst in ethyl alcohol as solvent at room temperature to obtain 3,4-difluorophenyl cyclohexanes or 4-alkyl-(3,4-difluorophenyl) cyclohexanes (VII). In the compounds (VII) are copresent a compound wherein the steric configuration of two substituents on the cyclohexane ring is of cis-form and a compound wherein the configuration is of trans-form, and among these, the trans-form compound has physical properties suitable as compounds similar to liquid crystals. As to a process for separating a cyclohexane derivertive expressed by the formula (I) from the compounds (VII), a known process such as recrystallization may be employed.

The compound of the present invention expressed by the formula (I) can be used as a novel liquid crystal composition by blending the compound with other liquid crystal compounds or liquid crystal compositions. When the compound is blended, at least one member may be selected from among the compounds expressed by the formula (I) and used. As to other liquid crystal compounds to be blended with the compound expressed by the formula (I), at least one compound included in known groups of compounds expressed by the formulas (iii–XXXV) shown below can be used. The content of the compound expressed by the formula (I) in a liquid crystal composition is preferably 1 to 30% by weight, more preferably 5 to 20% by weight.

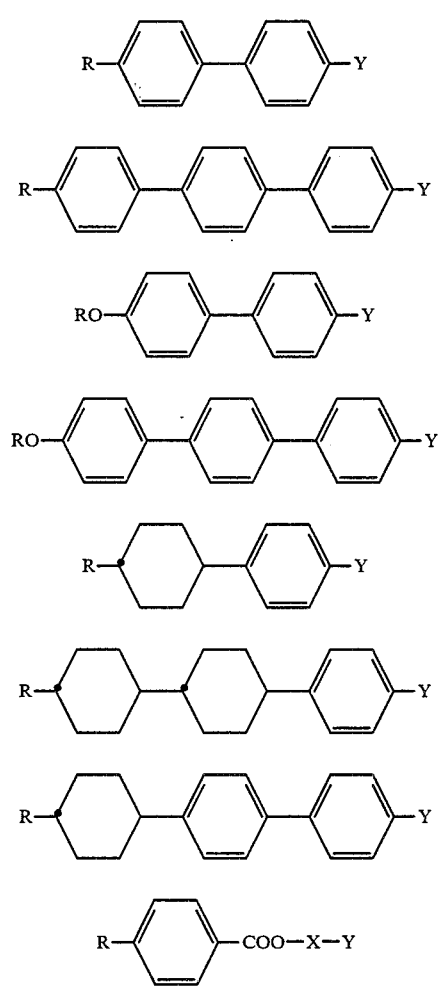

(iii)
(iv)
(v)
(vi)
(vii)
(viii)
(ix)
(x)

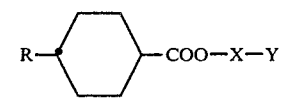

(xi)

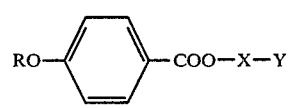

(xii)

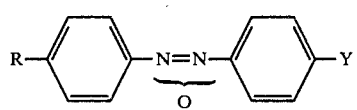

(xiii)

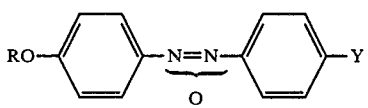

(xiv)

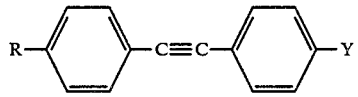

(xv)

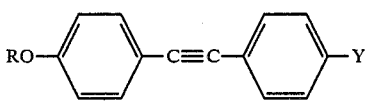

(xvi)

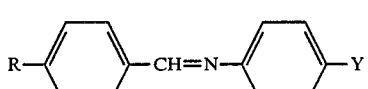

(xvii)

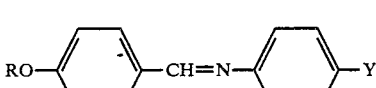

(xviii)

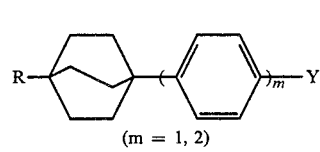

(m = 1, 2)

(xix)

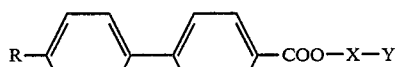

(xx)

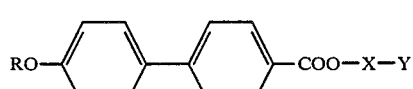

(xxi)

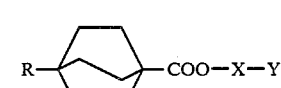

(xxii)

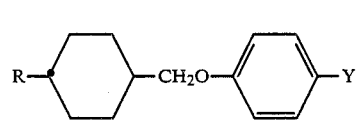

(xxiii)

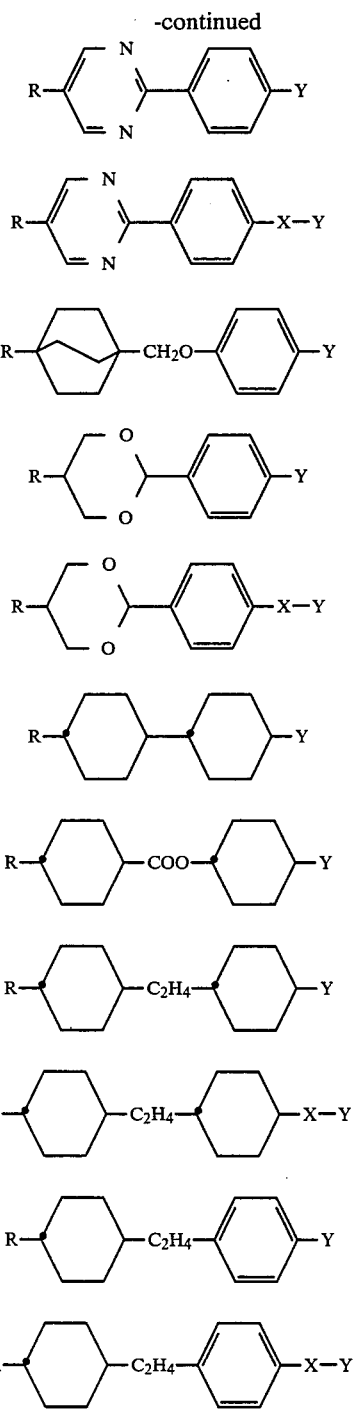

In the above formulas, R represents an alkyl group; X represents

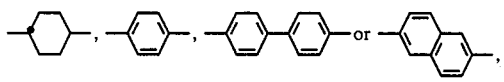

Y represents —C≡N, a halogen atom, an alkyl group or an alkoxy group, and the alkyl group of R may be the same as or different from the alkyl group of Y.

The compound of the present invention expressed by the formula (I) is a novel compound having superior physical properties i.e. an extremely low viscosity and a large dielectric anisotropy value. Further, by adding the compound expressed by the formula (I) to other liquid crystal compounds or liquid crystal compositions, it is possible to convert these liquid crystal compounds or liquid crystal compositions into liquid crystal compositions having a lower viscosity and a lower driving voltage.

The present invention will be described in more detail by way of Examples, but it should not be construed to be limited thereto.

EXAMPLE 1

Preparation of trans-4-pentyl-(3,4-difluorophenyl) cyclohexane

Mg (12.4 g, 0.510 g atom) was added to a solution of 3,4-difluorobromobenzene (97.8 g, 0.507 mol) dissolved in dried tetrahydrofuran (100 ml), followed by reacting the mixture while keeping it at 40° C. in nitrogen current for 2 hours, and then cooling down to 10° C. to obtain a reaction fluid 1. Into this reaction fluid 1 was poured a solution of 4-pentylcyclohexanone (85.8 g, 0.510 mol) dissolved in dried tetrahydrofuran (100 ml) at such a rate that the fluid temperature might not exceed 40° C., followed by reacting the mixture while keeping it at 50° C. for 2 hours, cooling down to room temperature to obtain a reaction fluid 2. To this reaction fluid 2 were added 6N-hydrochloric acid (50 ml) and water (200 ml), followed by extracting the deposited oily substance with n-heptane (200 ml), washing the extraction fluid with water till the washing water became neutral, and distilling off n-heptane to obtain an oily substance 1 corresponding to 3,4-difluoro-(4-pentylcyclohexane-1-ol) benzene. To this oily substance 1 was added potassium hydrogen surface (20 g), followed by keeping the mixture in nitrogen current at 180° C. for 2 hours to effect dehydration reaction, cooling down to room temperature, adding water (200 ml) and n-heptane (200 ml), separating the n-heptane layer, washing it with water till the washing water became neutral, and distilling off n-heptane to obtain an oily substance 2 corresponding to 3,4-difluoro-(4-pentylcyclohexane-1-yl) benzene. This oily substance 2 was dissolved in ethyl alcohol (100 ml), followed by adding a Raney Ni (6.0 g), carrying out a catalytic reduction reaction at 25° C. under the atmospheric pressure till absorption of hydrogen ceased, filtering off the Raney Ni, distilling off ethyl alcohol from the filtrate, distilling the remaining oily substance under reduced pressure to obtain a fraction having a b.p. of 115° C./2 mm Hg, which was then recrystallized from ethyl alcohol (100 ml) to obtain the objective trans-4-pentyl-(3,4-difluorophenyl) cyclohexane (23.8 g, 0.089 mol).

This product had a m.p. of −9.5° C. and a viscosity at 20° C. of 7 cp and its structure was confirmed according to IR and NMR.

EXAMPLE 2

Example 1 was repeated except that 4-pentylcyclohexanone used in Example 1 was replaced by 4-propylcyclohexanone (71.5 g, 0.510 mol), to obtain trans-4-propyl-(3,4-difluorophenyl) cyclohexane (20.8 g, 0.091 mol). This product had a m.p. of −15.4° C. and a viscosity at 20° C. of 77.2 cp.

By replacing 4-pentylcyclohexanone with cyclohexane or 4-alkylcyclohexanone having 1 to 4 or 6 to 10 carbon atoms in the alkyl group, the corresponding 3,4-difluorophenylcyclohexane or trans-4-alkyl-(3,4-difluorophenyl) cyclohexanes could be obtained.

EXAMPLE 3

A liquid crystal composition (A) consisting of 4 components, described below, has a N-I point of 72° C., a dielectric anisotropy value Δε of 11.6 and a viscosity at 20° C. of 27.8 cp, and when this composition was sealed in a TN cell of 10 μm in thickness, the resulting cell exhibited an operating threshold voltage of 1.75 V and a saturation voltage of 2.40 V.

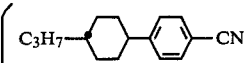

A liquid crystal composition (B) consisting of 85% by weight of the above liquid crystal composition (A) and 15% by weight of trans-4-pentyl-(3,4-difluorophenyl) cyclohexane prepared in Example 1 had a N-I point of 54.0° C., a dielectric anisotropy value Δε of 12.5 and a viscosity at 20° C. of 20.8 cp, and when the composition (B) was sealed in the above TN cell of 10 μm in thickness, the resulting cell exhibited an operating threshold voltage of 1.36 V and a saturation voltage of 2.00 V.

EXAMPLE 4

A liquid crystal composition (C) consisting of 85% by weight of the liquid crystal composition (A) used in Example 3 and 15% by weight of trans-4-propyl-(3,4-difluorophenyl) cyclohexane prepared in Example 2 had a N-I point of 44.0° C., a dielectric anisotrophy value Δε of +11.9 and a visocosity at 20° C. of 21.7 cp, and when the composition (C) was sealed in the above TN cell, the resulting cell exhibited an operating threshold voltage of 1.88 V.

As described above, it has been found that when the compound of the present invention is used as a component of a liquid crystal composition, it has an effectiveness of notably reducing the viscosity and the driving voltage of the resulting liquid crystal composition.

What we claim is:

1. A cyclohexane derivative having the formula

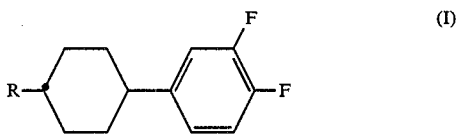

wherein R represents an alkyl group of 1 to 10 carbon atoms.

2. A liquid crystal composition having at least two components at least one of which is a compound expressed by the formula (I) set forth in claim 1.

3. A compound according to claim 1 wherein R is $C_5H_{11}$.

4. A compound according to claim 1 wherein R is $C_3H_7$.

5. A liquid crystal composition comprising 85% by weight of a composition consisting of:
   24% by weight of trans-4-propyl-(4'cyanophenyl)-cyclohexane;
   36% by weight of trans-4-pentyl-(4'cyanophenyl)-cyclohexane;
   25% by weight of trans-4-heptyl-(4'cyanophenyl)-cyclohexane;
   15% by weight of trans-4-pentyl-(4"cyanobiphenyl)-cyclo-hexane; and,
   15% by weight of trans-4-pentyl-(3,4-difluorophenyl)-cyclo-hexane.

6. A liquid crystal composition comprising 85% by weight of a composition consisting of:
   24% by weight of trans-4-propyl-(4'-cyanophenyl)-cyclo-hexane;
   36% by weight of trans-4-pentyl-(4'-cyanophenyl)-cyclo-hexane;
   25% by weight of trans-4-heptyl-(4'-cyanophenyl)-cyclo-hexane;
   15% by weight of trans-4-pentyl-(4"-cyanobiphenyl)-cyclo-hexane; and,
   15% by weight of trans-4-propyl-(3,4-difluorophenyl)-cyclo-hexane.

7. A process of reducing the viscosity and operating voltage of a liquid crystal composition comprising adding a cyclohexane derivative expressed by the formula:

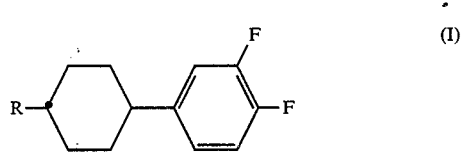

to a liquid crystal composition, wherein R represents an alkyl group of 1 to 10 atoms.

8. A compound having the formula:

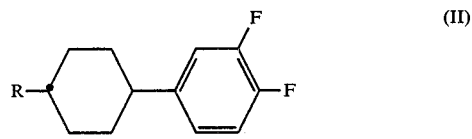

where R represents a hydrogen atom.

9. A liquid crystal composition including at least two components at least one of which is a compound expressed by the formula (II) set forth in claim 8.

10. A process of reducing the viscosity and operating voltage of a liquid crystal composition comprising adding a cyclohexane derivative expressed by the formula:

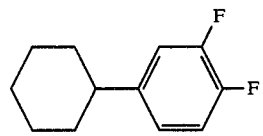

to a liquid crystal composition.

* * * * *